United States Patent
Rohlen

(10) Patent No.: US 7,682,089 B2
(45) Date of Patent: Mar. 23, 2010

(54) SYSTEM AND METHOD FOR POSITIONING A PROBE

(76) Inventor: Brooks H. Rohlen, P.O. Box 20476, Stanford, CA (US) 94309

(*) Notice: Subject to any disclaimer, the term of this patent is extended or adjusted under 35 U.S.C. 154(b) by 243 days.

(21) Appl. No.: 11/839,517

(22) Filed: Aug. 15, 2007

(65) Prior Publication Data
US 2009/0046980 A1 Feb. 19, 2009

(51) Int. Cl.
*G02B 6/36* (2006.01)
*G02B 6/26* (2006.01)

(52) U.S. Cl. ........................ 385/88; 385/39

(58) Field of Classification Search ............ 385/88, 385/39
See application file for complete search history.

(56) References Cited

U.S. PATENT DOCUMENTS

| | | | | |
|---|---|---|---|---|
| 3,941,121 | A | | 3/1976 | Olinger |
| 4,435,037 | A | * | 3/1984 | Abramson et al. ............ 385/90 |
| 4,588,256 | A | * | 5/1986 | Onstott et al. ................. 385/87 |
| 4,589,404 | A | * | 5/1986 | Barath et al. ................ 600/108 |
| 4,681,398 | A | * | 7/1987 | Bailey et al. ................... 385/79 |
| 4,682,848 | A | * | 7/1987 | Cairns et al. ................... 385/69 |
| 4,754,328 | A | * | 6/1988 | Barath et al. ................... 348/67 |
| 4,959,063 | A | | 9/1990 | Kojima |
| 5,011,473 | A | | 4/1991 | Gatturna |
| 5,178,153 | A | * | 1/1993 | Einzig ........................ 600/505 |
| 5,251,276 | A | * | 10/1993 | Berkey et al. ................. 385/43 |
| 5,405,474 | A | * | 4/1995 | Berkey et al. ............... 156/250 |
| 5,562,610 | A | | 10/1996 | Brumbach |
| 5,752,518 | A | | 5/1998 | McGee |
| 6,053,871 | A | | 4/2000 | Cockburn |
| 6,179,611 | B1 | | 1/2001 | Everett |
| 6,231,568 | B1 | * | 5/2001 | Loeb et al. ..................... 606/15 |
| 6,325,883 | B1 | * | 12/2001 | Backer et al. ............. 156/275.5 |
| 6,331,178 | B1 | * | 12/2001 | Loeb et al. ..................... 606/13 |
| 6,485,413 | B1 | | 11/2002 | Boppart |
| 6,514,277 | B1 | * | 2/2003 | Lilge et al. ..................... 607/88 |
| 6,551,302 | B1 | * | 4/2003 | Rosinko et al. ............. 604/505 |
| 6,554,794 | B1 | * | 4/2003 | Mueller et al. ........... 604/95.04 |
| 6,564,087 | B1 | * | 5/2003 | Pitris et al. .................. 600/478 |
| 6,993,376 | B2 | * | 1/2006 | Testardi ...................... 600/478 |
| 7,189,226 | B2 | * | 3/2007 | Auld et al. ..................... 606/11 |
| 7,204,826 | B2 | | 4/2007 | Tremaglio |
| 7,524,316 | B2 | * | 4/2009 | Hennings et al. ................ 606/7 |
| 2001/0023346 | A1 | * | 9/2001 | Loeb .......................... 604/508 |
| 2002/0037149 | A1 | * | 3/2002 | Chen .......................... 385/147 |
| 2003/0114842 | A1 | * | 6/2003 | DiStefano ....................... 606/7 |
| 2003/0163016 | A1 | * | 8/2003 | Testardi .......................... 600/2 |
| 2004/0019280 | A1 | * | 1/2004 | Waner et al. ................. 600/466 |
| 2004/0086230 | A1 | * | 5/2004 | Lewandowski et al. ....... 385/46 |
| 2005/0004453 | A1 | * | 1/2005 | Tearney et al. .............. 600/427 |
| 2005/0033389 | A1 | * | 2/2005 | Auld et al. ..................... 607/89 |
| 2006/0241503 | A1 | * | 10/2006 | Schmitt et al. .............. 600/478 |
| 2007/0148782 | A1 | * | 6/2007 | Pawliszyn ................... 436/514 |

(Continued)

*Primary Examiner*—K. Cyrus Kianni
(74) *Attorney, Agent, or Firm*—M. Dean Matthews

(57) ABSTRACT

An adapter couples a length of optical fiber to a hollow probe and to an optical coherence tomography instrument. The length of optical fiber may be greater than the length of the adapter itself. The optical fiber is fixed to an optical coupler at a proximal end of the adapter and may be maintained in a curved configuration by features located in an internal cavity of the adapter. An optical fiber advance mechanism be used to advance and/or retract the length of optical fiber to align it within the hollow probe.

12 Claims, 9 Drawing Sheets

U.S. PATENT DOCUMENTS

2007/0255264 A1* 11/2007 Hickingbotham ............. 606/2
2007/0270788 A1* 11/2007 Nahen et al. ................. 606/15
2008/0021527 A1* 1/2008 Hennings et al. ............. 607/89

* cited by examiner

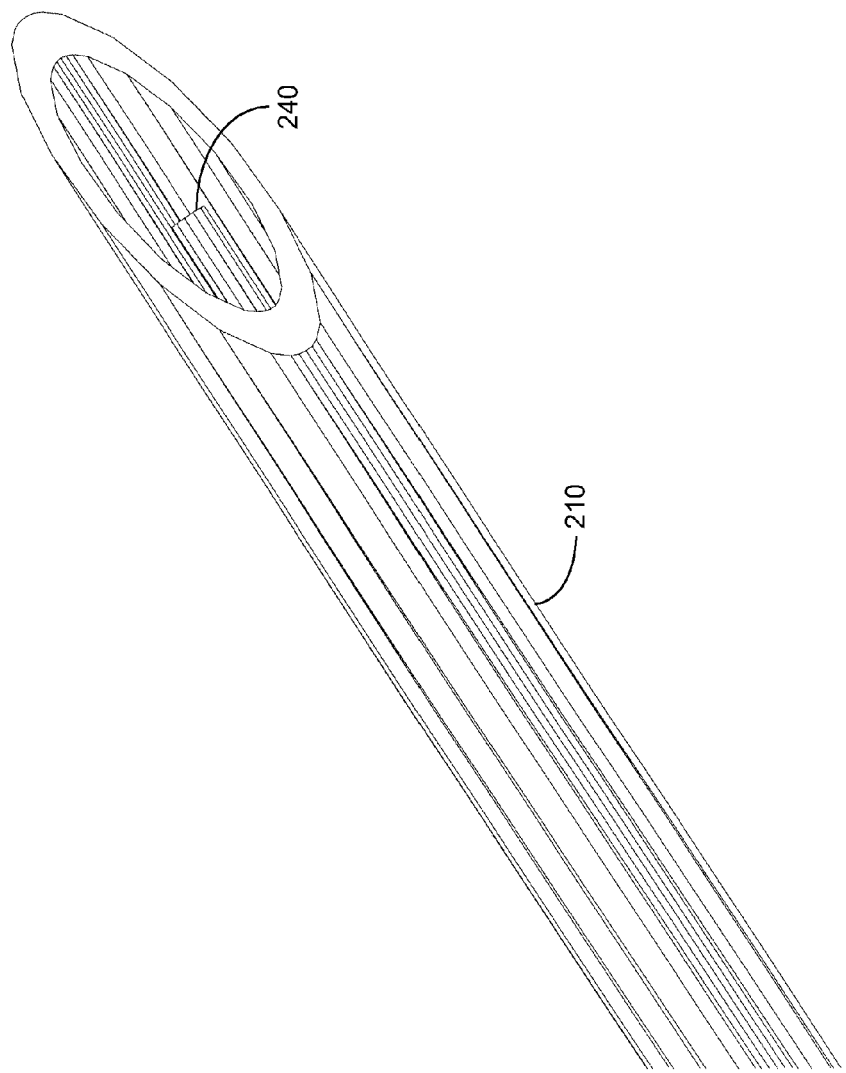

SYSTEM AND METHOD FOR POSITIONING A PROBE

BACKGROUND OF THE INVENTION

1. Field of the Invention

The present invention relates to medical probes. In particular, the invention relates to a system for positioning a medical probe.

2. Description of Related Art

There are many medical procedures that require the insertion of a probe or needle along a specific path or to a specific location within the human body. The execution of these procedures often relies solely upon the vision and tactile sense of the practitioner For example, a hypodermic needle may be inserted into the jugular vein of a patient as a prelude to catheritization. Incorrect insertion of a hypodermic needle into the jugular may result in a punctured lung or other complications, thus, a post catheritization X-ray is frequently taken to verify the success of the procedure.

Realtime visual information (e.g., ultrasound imaging) regarding internal tissue structures is helpful in avoiding complications during medical procedures; however, realtime imaging techniques may make a procedure significantly more complex. Also, additional personnel or an increased amount of time may also be required.

Optical coherence tomography (OCT) is frequently used for realtime imaging and may be integrated with a number of instruments. Such integrated instruments typically require sterilization before reuse and thus are not well suited to high-volume procedures.

Thus, a need exists for a system and method for positioning a probe that does not require sterilization before reuse. There is also a need for a system and method for positioning a probe that is suitable for use in high-volume procedures.

BRIEF SUMMARY OF THE INVENTION

The present invention provides an adapter that couples one or more optical fibers to a hollow probe. The adapter contains a length of optical fiber that is longer than the adapter itself. The optical fiber may be extended into the hollow probe.

In one embodiment of the invention the length of optical fiber is fixed to an optical coupler at a proximal end of the adapter and is maintained in a curved configuration by features located in an internal cavity of the adapter.

In further embodiment, a conical needle adapter at the distal end of the adapter is configured to accept a hypodermic needle. The conical adapter may have a Luer taper.

In another embodiment, a pair of rollers are used to advance the length of optical fiber. The rollers may be composite with a hard core and soft surface, and may also be sealed with in the adapter.

BRIEF DESCRIPTION OF THE DRAWINGS

FIG. 2B shows an alignment of an optical fiber at the tip of an attached hypodermic needle in accordance with an embodiment of the present invention.

DETAILED DESCRIPTION OF THE INVENTION

Figure 1A:
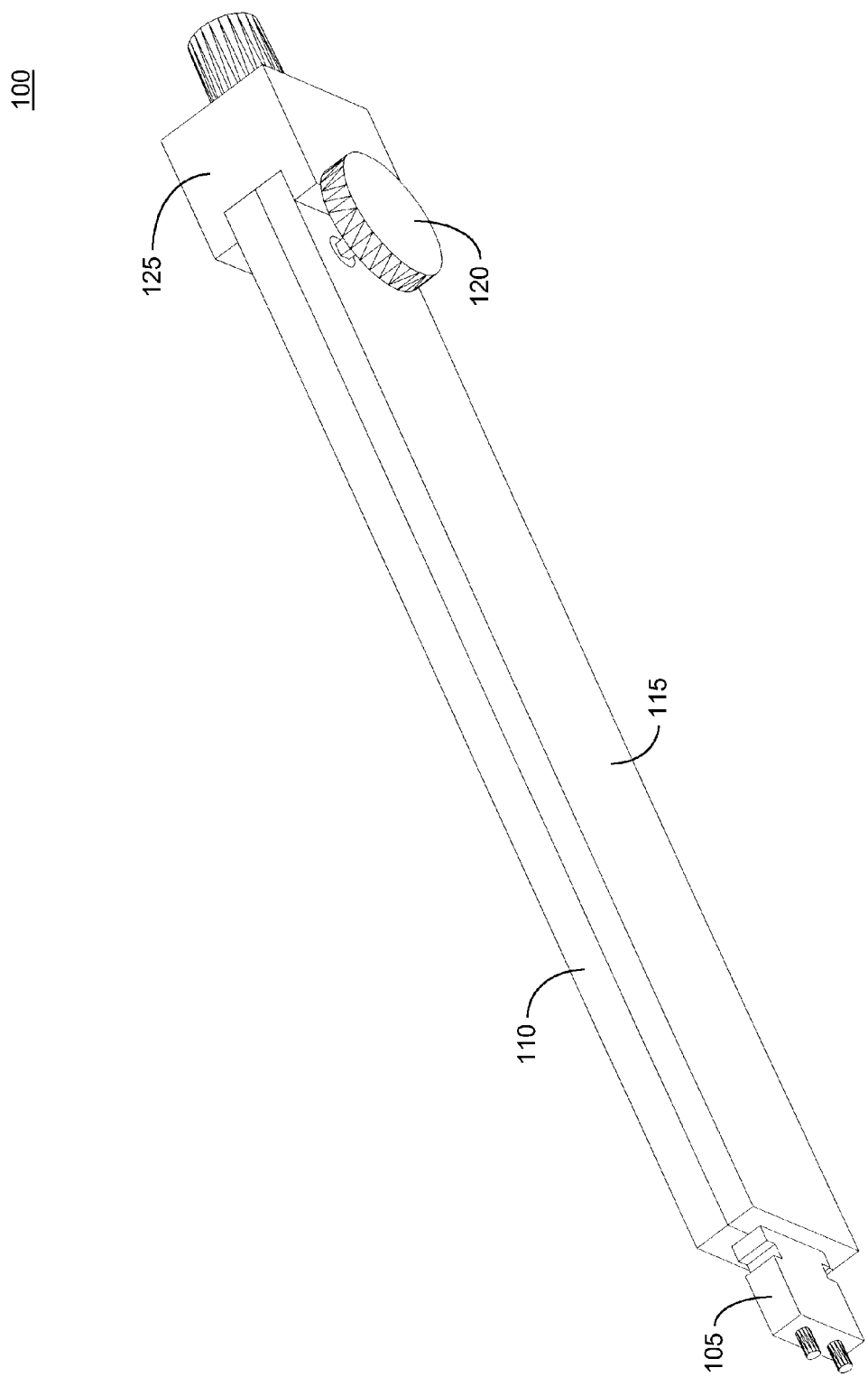
FIG. 1A shows a top perspective view of an optical probe adapter in accordance with an embodiment of the present invention.

FIG. 1A shows a top perspective view 100 of an embodiment of an optical probe adapter. The optical probe adapter 100 has a optical fiber coupler 105 at the proximal end and a probe coupler 125 at the distal end. A fiber receiver 110 and cover 115 serve as a handle and also as a housing for an optical fiber, or optical fiber bundle.

Figure 1B:
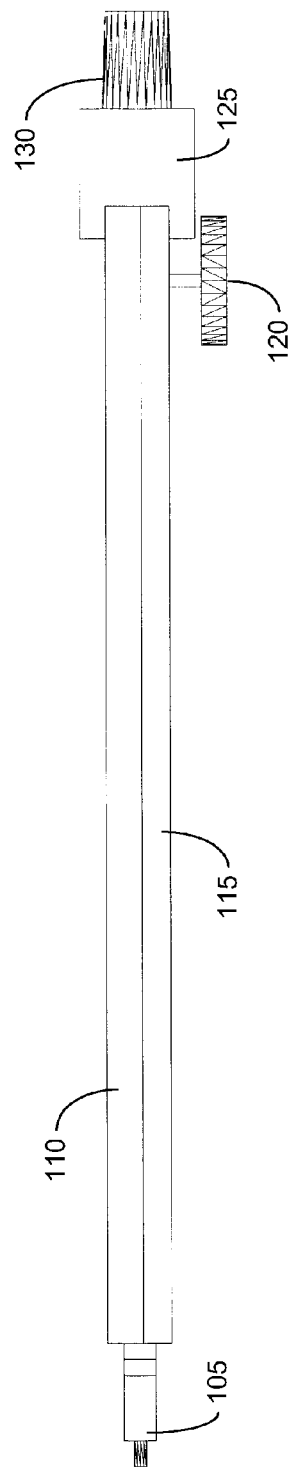
FIG. 1B shows a top view of the optical probe adapter of FIG. 1A.

FIG. 1B shows a top view 101 of the optical probe adapter of FIG. 1A. A knob 120 provides a means of advancing or retracting the fiber housed within the optical fiber adapter. The probe coupler 125 has a conical taper 130 that accepts a probe (e.g., hypodermic needle). The conical taper 130 may be a Luer taper. A Luer lock or other interlocking connector may be used in conjunction with the probe coupler 125. However, since the optical probe adapter is only temporarily coupled to the probe, ease of removal is desired so that the probe position is not perturbed during removal.

Figure 1C:
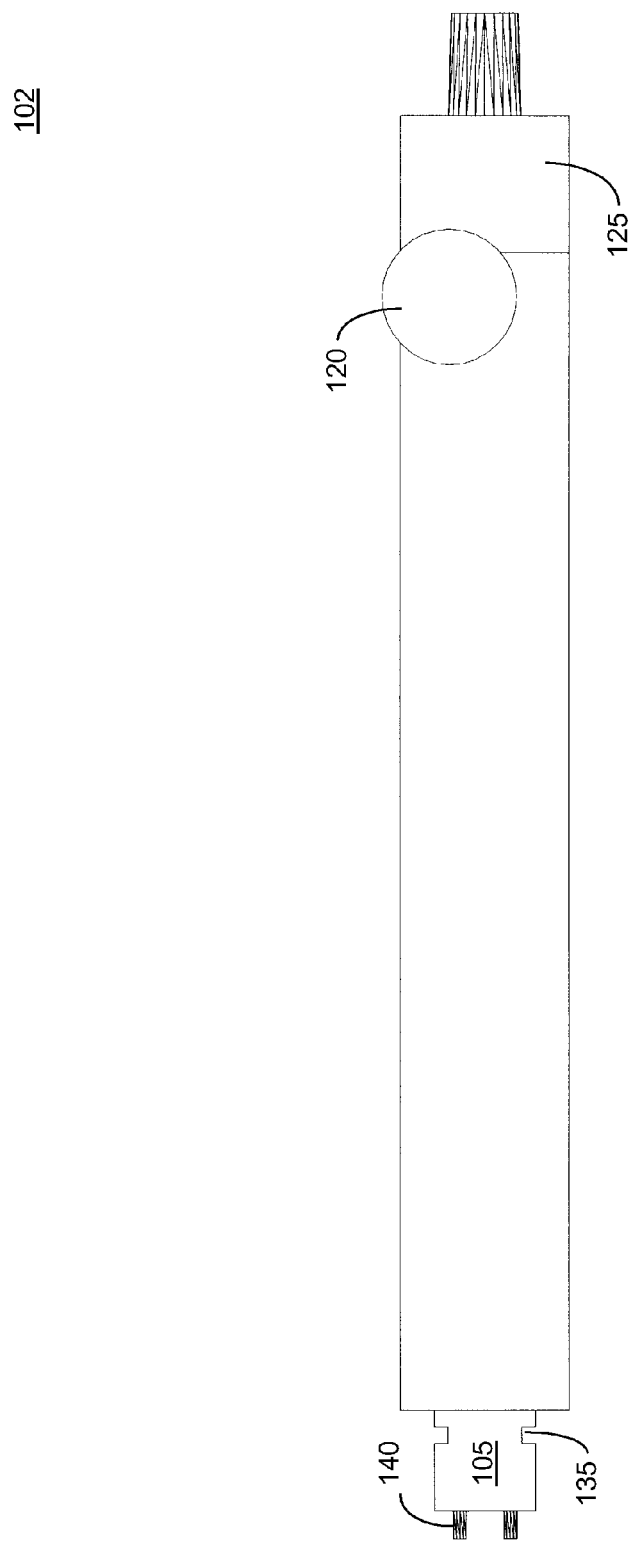
FIG. 1C shows a front view of the optical probe adapter of FIG. 1A.

FIG. 1C shows a front view 102 of the optical probe adapter of FIG. 1A. The optical fiber coupler 105 has two optical fiber terminals 140. In alternative embodiments, the optical fiber coupler 105 may have a greater or lesser number of optical fiber terminals.

The optical fiber coupler 105 has two detents 135 that provide a means for locking the coupler into a mated connector. There are many types of optical fiber couplers that may be used. However, most conventional optical fiber adapters are designed for many make-and-break connections. For disposable or single use optical probe adapters, it is preferable that the optical fiber coupler 105 be kept mechanically simple. Any complexity associated with obtaining a reliable connection should reside in the non-disposable component with which the optical coupler 105 may be mated.

Figure 1D:
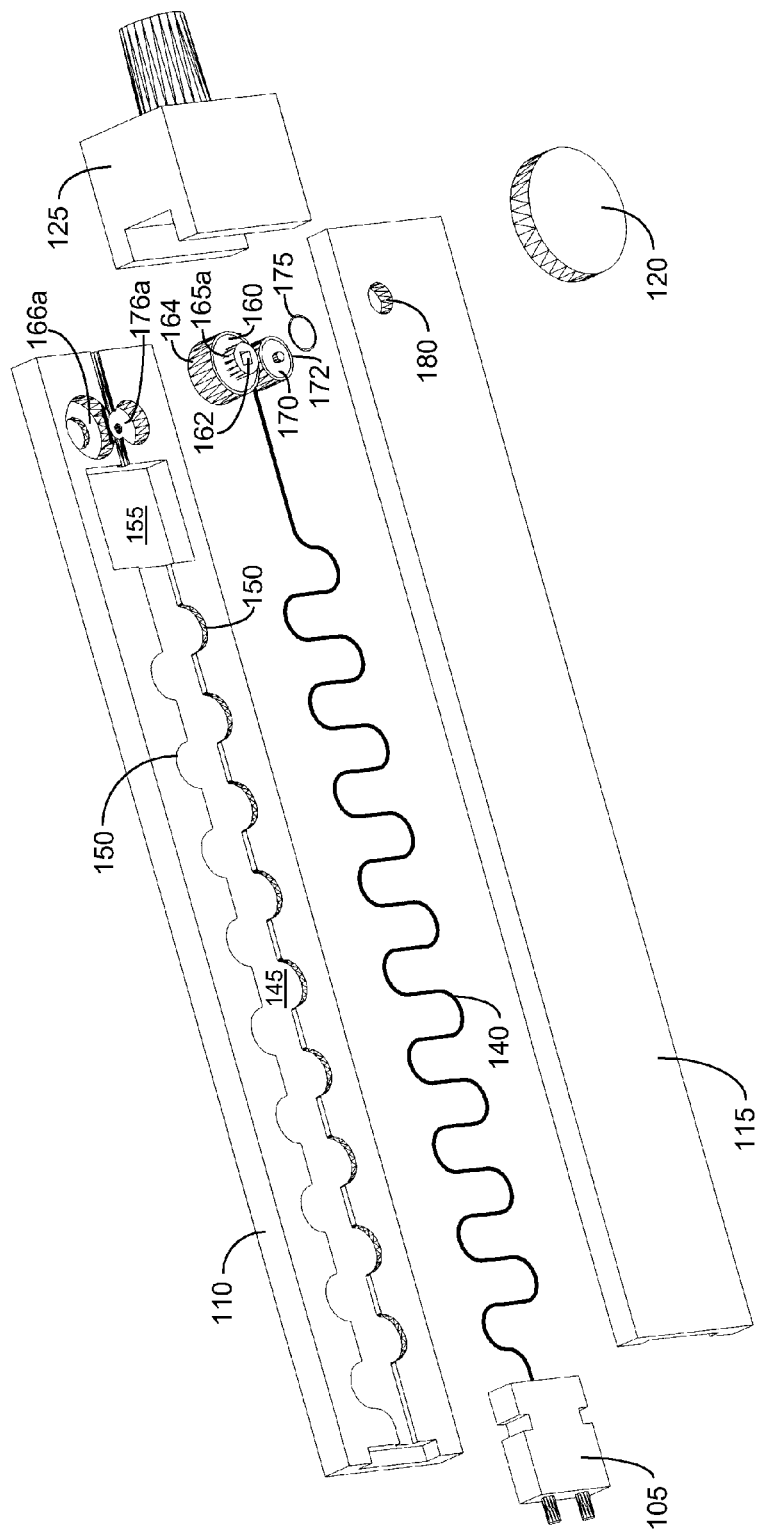
FIG. 1D shows a front perspective exploded view of the optical probe adapter of FIG. 1A.

FIG. 1D shows a front perspective exploded view 103 of the optical probe adapter of FIG. 1A. An optical fiber bundle 140 is connected to the optical fiber coupler 105. In other embodiments, a single fiber may be substituted for the optical fiber bundle 140. The optical fiber bundle 140 resides in a cavity 145 in the receiver 110. The cavity 145 has a series of radiused edges 150 that allow the optical fiber bundle to be compactly housed.

In general, housing of the optical fiber bundle 140 requires that at least a portion of the optical fiber bundle 140 be stored in a curved configuration. For efficient packing at least one portion will typically have an arc of at least 90 degrees and may have a variable radius. The length of the optical bundle that is ultimately advanced through the probe coupler 125 is derived from the straightening of a curved portion. Although spirals or coils may also be used as housing configurations for the optical fiber bundle 140, the serpentine configuration shown in FIG. 1D has the advantage of avoiding twisting of the fiber during assembly and use. An arc length of 180 degrees is used in the serpentine configuration.

The optical fiber 140 is advanced and retracted by a drive roller 160 acting against a pinch roller 170. The driver roller 160 has a soft outer covering 164 that reduces localized stress in the area of contact with the optical fiber bundle 140. Similarly, the pinch roller 170 has a soft outer covering 172. The conformation of the soft outer coverings 164 and 172 with the optical fiber bundle 140 increases the contact area and the overall friction that provides the force for advancing and retracting the optical fiber bundle 140. In alternative embodiments other fiber advancing mechanisms may be used.

An optional gasket 175 provides a seal between the face of the drive roller 160 and the cover 115. Alternatively, a seal may be established between the drive roller axle portion 165*a* and the surface of the drive roller axle bore 180. A keyway 162 in the driver roller bearing portion accepts a key 168 (FIG. 1E) that transmits torque applied to the knob 120.

The receiver 110 includes a drive roller axle bearing cavity 166*a* and a pinch roller axle bearing cavity 176*a*. The drive roller axle bearing cavity 166*a* and a pinch roller axle bearing cavity 176*a* are blind cavities; however, through holes may be used in other embodiments.

An optional storage cavity 155 provides a volume adjacent to drive roller 160 and pinch roller 170. Upon retraction, the optical fiber bundle 140 will not easily resume its initial configuration and the storage cavity provides a local storage site. Although retraction may not be required to complete a particular medical procedure, it may be desirable to retract the optical fiber 140 for easier handling.

Figure 1E:
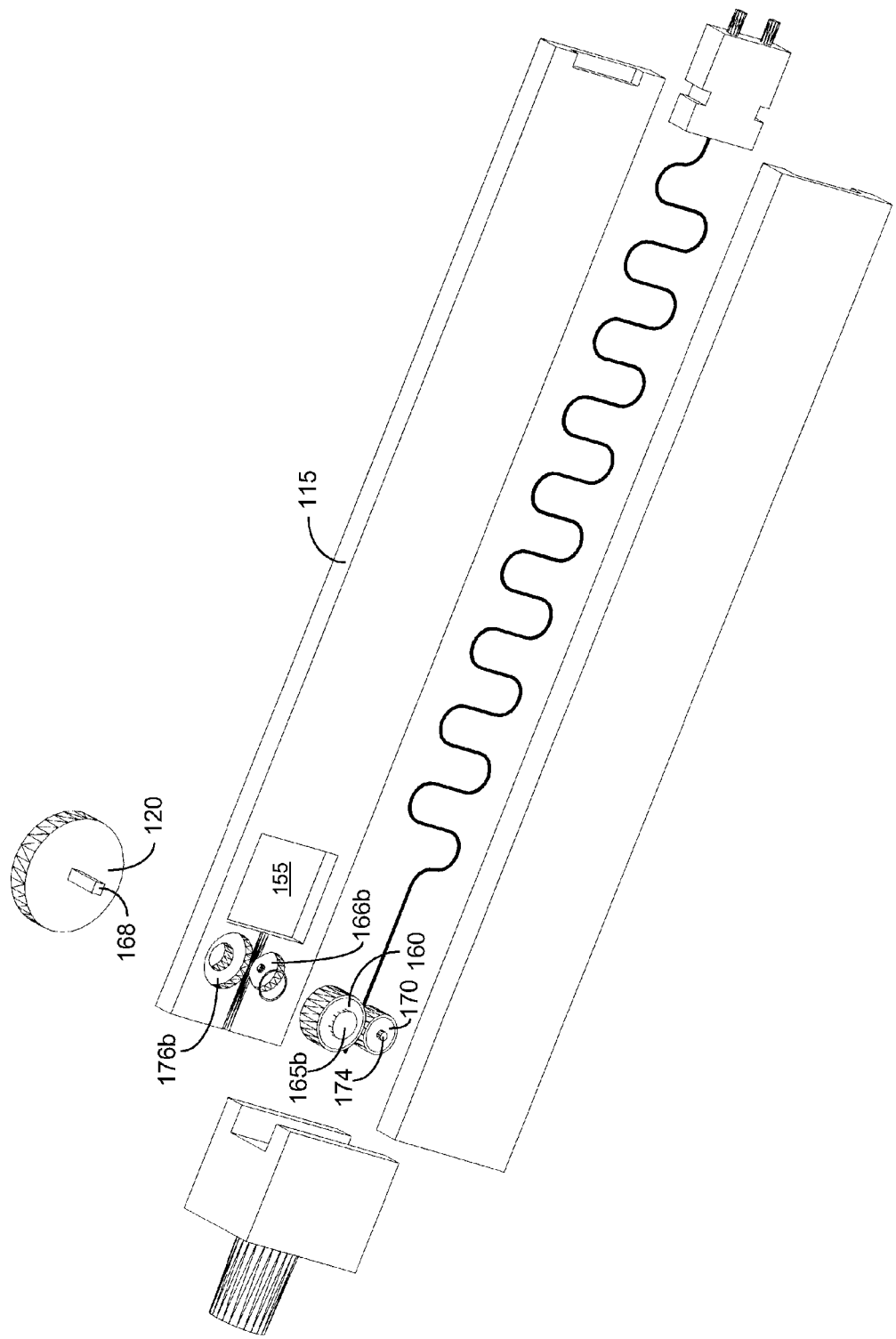
FIG. 1E shows a back perspective exploded view of the optical probe adapter of FIG. 1A.

FIG. 1E shows a back perspective exploded view of the optical probe adapter of FIG. 1A. The cover 115 has an optional storage cavity 155 similar to that associated with the receiver 110. The cover 115 includes a drive roller axle bearing cavity 166*b* and a pinch roller axle bearing cavity 176*b*.

An axle 174 supports pinch roller 170. Since it is desirable to minimize resistance to rotation, it is preferable that axle 174 not be fixed to pinch roller 170. In contrast, drive roller axle portions 165*a* and 165*b* are integrated with drive roller 160. A minimum resistance to rotation is desirable in the drive roller 160 so that it can hold the optical fiber 140 in a fixed position after alignment.

A key 168 transmits the torque applied to knob 120 to the pinch roller 160. The knob 120, key 168, and drive roller 160 may be fabricated as an integrated unit or as components that are separable in whole or in part. A removable knob 120 and key 168 are desirable when they would interfere with positioning of an attached probe after extension of the optical fiber bundle 140.

Figure 2A:
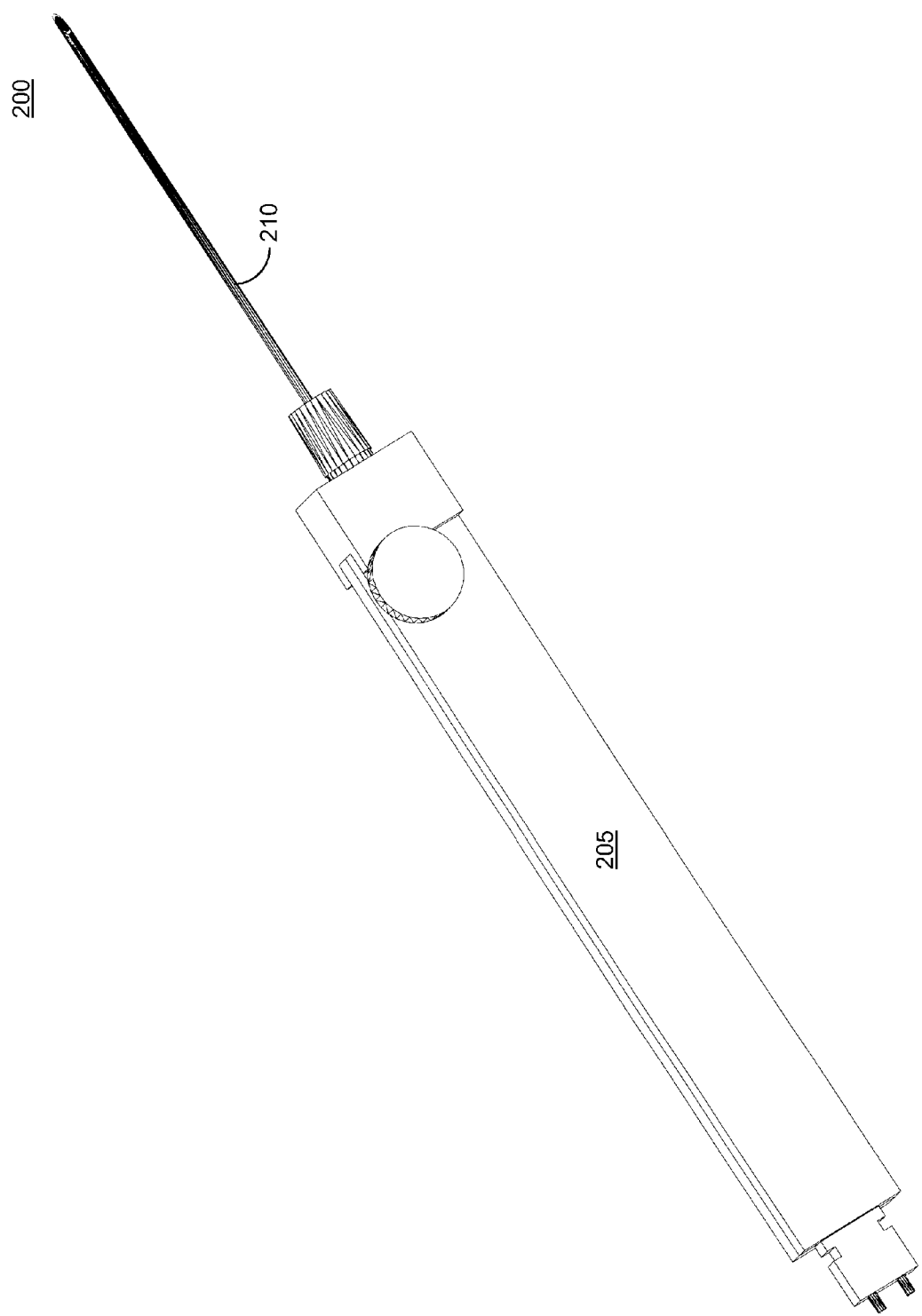
FIG. 2A shows an optical probe adapter with an attached hypodermic needle in accordance with an embodiment of the present invention.

FIG. 2A shows a perspective view 200 of an embodiment of an optical probe adapter 205 with an attached hypodermic needle 210. In alternative embodiments a cylindrical cross-section may be substituted for the rectangular cross-section. Although the rectangular cross-section minimizes the size of the optical probe adapter, the radial symmetry of a cylindrical cross-section may provide greater ease of handling.

Although the hypodermic needle 210 is shown as shorter than the optical probe adapter 205, the hypodermic needle 210 may be longer than the optical probe adapter 205. For example, the optical probe adapter may have a length of about 10 centimeters and the hypodermic needle may have a length of 10 to 15 centimeters. FIG. 2B shows an alignment of an optical fiber 240 at the tip of the attached hypodermic needle 210 of FIG. 2A.

Figure 3:
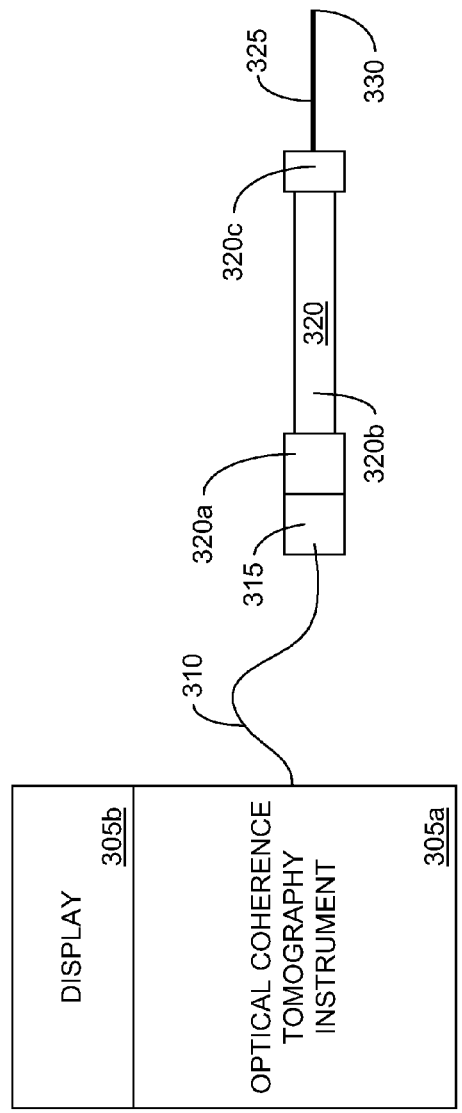
FIG. 3 shows a diagram of a probe positioning system in accordance with an embodiment of the present invention.

FIG. 3 shows a diagram 300 of an embodiment of a probe positioning system. An optical coherence tomography (OCT) instrument 305*a* provides illumination and receives a reflected light signal through an optic fiber 310 that has a connector 315. The optical coherence tomography (OCT) instrument 305*a* may be a battery powered portable instrument. The connector 315 mates to the optical fiber adapter 320 via the fiber optic coupler 320*a*. The housing 320*b* contains a length of optical fiber that may be advanced to align with the distal tip 330 of a probe 325.

Figure 4:
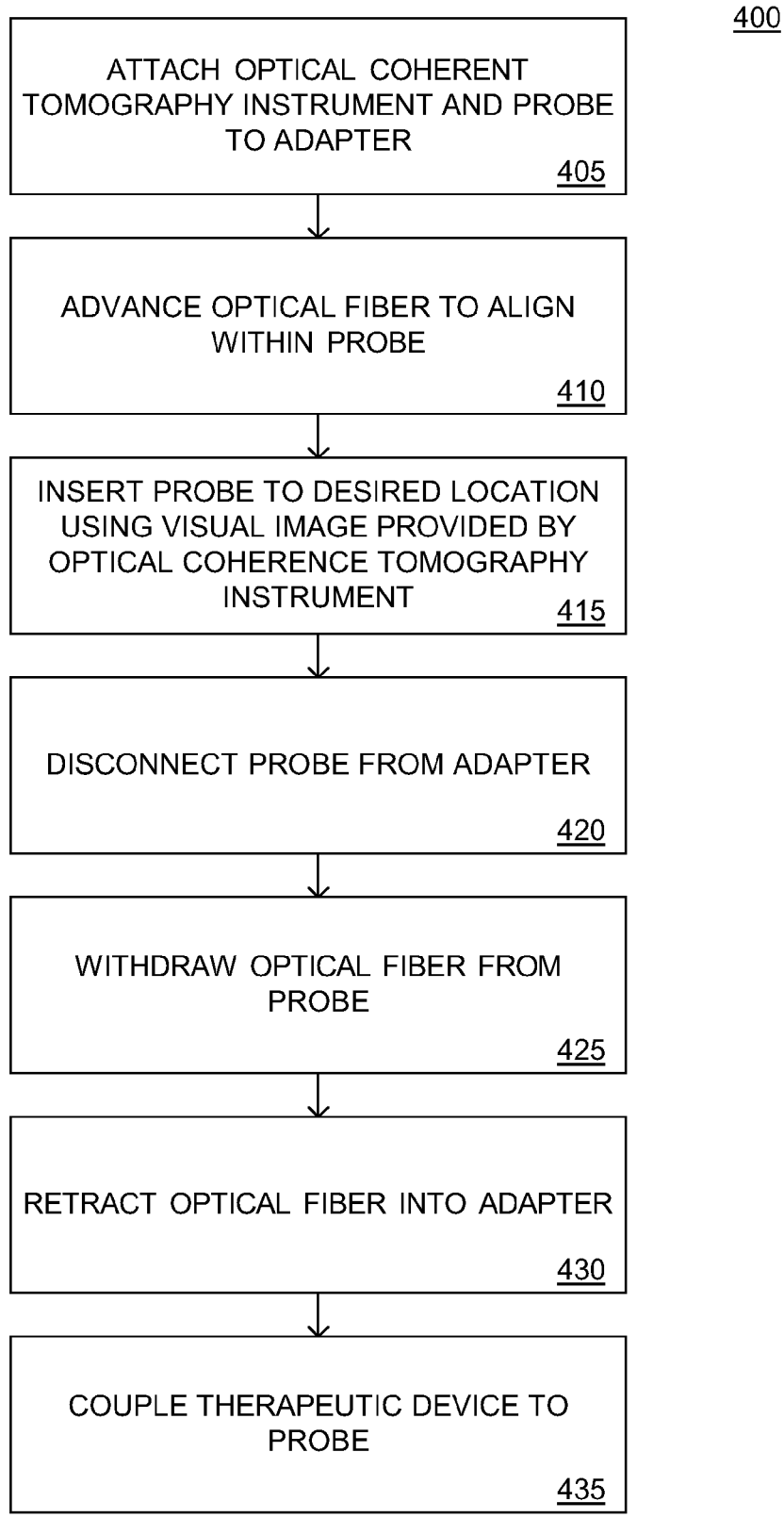
FIG. 4 shows a flow chart diagram for a method embodiment of the present invention.

FIG. 4 shows a flow chart diagram 400 for an embodiment of a method for inserting a probe using a system similar to that shown in FIG. 3. At step 405 an optical coherence tomography (OCT) instrument is attached to an optical fiber probe adapter. This connection will typically be made using a cable. A probe is also attached to the optical fiber probe adapter. The probe may be connected by a simple press fit or it may be connected by a mechanical interlock such as a thread, bayonet, or twist lock.

At step 410 the optical fiber is advanced from the optical fiber probe adapter and aligned within the probe. Generally, the optical fiber will be advanced to the vicinity of the distal tip of the probe. However, if a portion of the probe is transparent, the optical fiber may reside entirely within the probe.

At step 415 the probe is inserted to the desired location using the visual image provided by the OCT instrument. Probes for procedures such as catheterization and nerve blocks may be inserted with the optical fiber probe adapter.

At step 420 the probe is disconnected from the optical fiber probe adapter. The probe may be disconnected without changing the alignment of the optical fiber within the probe, or the optical fiber may be realigned prior to being disconnected.

At step 425 the optical fiber is withdrawn from the probe. At step 430 the optical fiber is retracted into the probe. Retraction of the optical fiber into the probe is an optional step and may be performed prior to withdrawal of the optical fiber from the probe. At step 435 a therapeutic device such as a syringe or a catheter is coupled to the probe.

While the invention has been described in detail with reference to preferred embodiments thereof, it will be apparent to one skilled in the art that various changes can be made, and equivalents employed, without departing from the scope of the invention.

What is claimed:

1. An optical fiber probe adapter comprising:
    an optical fiber housing;
    a cavity disposed within said optical fiber housing, wherein said cavity comprises plurality of curved surfaces;
    a fiber optic coupler connected to a proximal end of said optical fiber housing;
    a length of optical fiber contained within said optical fiber housing and coupled to said fiber optic coupler, wherein said optical fiber comprises a plurality of arcuate segments approximately conforming to said plurality of curved surfaces;
    a probe coupler connected to a distal end of said optical fiber housing; and
    an optical fiber advance mechanism coupled to said housing.

2. The optical fiber probe adapter of claim 1 wherein at least one portion of said length of optical fiber has an arc length of at least 90 degrees.

3. The optical fiber probe adapter of claim 2 wherein at least one portion of said length of optical fiber has an arc length of at least 180 degrees.

4. The optical fiber probe adapter of claim 1 wherein said optical fiber advance mechanism comprises a pinch roller.

5. The optical fiber probe adapter of claim 1 wherein said probe coupler comprises a portion with a conical taper.

6. The optical fiber probe adapter of claim 1 wherein said length of optical fiber is contained within a cavity having at least one surface feature for housing said optical fiber in a curved configuration.

7. The optical fiber probe adapter of claim 1 further comprising a cavity adjacent to said optical fiber advance mechanism for receiving said optical fiber upon retraction.

8. A system for positioning a probe, said system comprising:
- an optical coherence tomography instrument;
- a display coupled to said optical coherence tomography instrument;
- an optical fiber probe adapter coupled to said optical coherence tomography instrument by a cable, wherein said optical fiber probe adapter further comprises: an optical fiber housing; a cavity disposed within said optical fiber housing, wherein said cavity comprises a plurality of curved surfaces; a fiber optic coupler connected to a proximal end of said optical fiber housing; a length of optical fiber contained within said optical fiber housing and coupled to said fiber optic coupler, wherein said optical fiber comprises a plurality of arcuate segments Approximately conforming to said plurality of curved surfaces;
- a probe coupler connected to a distal end of said optical fiber housing; and
- an optical fiber advance mechanism coupled to said housing;
- and a probe coupled to said optical fiber probe adapter.

9. The system of claim 8 wherein said probe is a hypodermic needle.

10. The system of claim 8 wherein at least one portion of said length of optical fiber has an arc length of at least 90 degrees.

11. The system of claim 8 wherein said optical fiber advance mechanism comprises a pinch roller.

12. The system of claim 8 wherein said probe coupler comprises a portion with a conical taper.

* * * * *